United States Patent [19]

Nielsen

[11] Patent Number: 4,936,898

[45] Date of Patent: Jun. 26, 1990

[54] ATOMIZED ELEMENTAL MOSS KILLER

[76] Inventor: James W. Nielsen, P.O. Box 6669, Brookings, Oreg. 97415

[21] Appl. No.: 849,745

[22] Filed: Apr. 9, 1986

[51] Int. Cl.$^5$ .................... A01N 59/06; A01N 59/20; A01N 59/16; A01N 59/00

[52] U.S. Cl. ........................................... 71/65; 71/11; 71/32; 71/54; 71/61; 71/67; 71/DIG. 1

[58] Field of Search ........................ 71/65, 67, DIG. 1

[56] References Cited

U.S. PATENT DOCUMENTS

| | | | |
|---|---|---|---|
| 3,479,130 | 11/1969 | Rapaport | 21/61 |
| 3,494,727 | 2/1970 | Rapaport | 21/61 |
| 3,964,893 | 6/1976 | Everingham | 71/65 |
| 4,276,732 | 7/1981 | Nielsen | 52/517 |

Primary Examiner—Glennon H. Hollrah
Assistant Examiner—K. Konstas

[57] ABSTRACT

A method is disclosed for killing moss growing on a moss-covered surface by sprinkling in dry or wet form a moss-killing powder containing an atomized elemental metal which slowly dissolves with water to form a biocidal solution which kills moss. In the preferred embodiment, a moss-killing powder dry or wet consists essentially of finely powdered atomized elemental zinc and copper mixed with a powdered, dispersible carrier material, such as silia clay, to which the metal particles adhere. The moss-killing powder is sprinkled on a wetted moss-covered surface dry or mixed in a slurry of water and sprinkled wet which causes the powder to initially adhere to the surface. Upon contact with rainwater, or tap water or dew the carrier soaks up water and slowly disintegrate, retaining the metal particles in close proximity so that they electrolytically react with the rainwater or tap water or dew to produce a biocidal solution which kills moss. Gradually the carrier disperses or dissolves and disappears. The elemental metal powder and granular material are combined in particle sizes and proportions such that metal ions are gradually released over a long duration, thereby producing a moss-killing effect which continues for at least one year after a single application.

7 Claims, No Drawings

ATOMIZED ELEMENTAL MOSS KILLER

BACKGROUND OF THE INVENTION

The invention relates generally to removal and prevention of undesired growths of moss and the like from rooftops, buildings and other outside surfaces exposed to the atmosphere and more particularly to an improved method and product for biocidal treatment of such surfaces.

In very moist climates, the growth of moss, mildew, and other organisms on shaded surfaces, such as rooftops, buildings, walkways, patios, driveways, and grass, is a problem. Such growths are unsightly, do not permit the surface to dry, and can cause a variety of problems depending on the nature of the surface. In particular, moss growth on rooftops does not allow the roof to dry properly and eventually causes accelerated decomposition of the shingles. This permits water leakage which can damage the roof support structure and ceiling materials below. The resultant damage is very expensive to repair. Similarly, moss growth along expansion joints and in cracks on concrete surfaces, such as patios and driveways, is unsightly, fosters additional undesired microbial growth, and accelerates decomposition of the concrete. It can also be slippery when wet, increasing the risk of injury to users. Moss growth in lawns and in gardens also is unsightly, competes with the grass, and fosters weed and other undesired microbial growth. Consequently, it is desirable to kill moss growing on each of these surfaces and to prevent its return.

Manual removal of moss from rooftops is difficult, dangerous, and provides only a temporary solution to the problem. The moss regrows within a short time from spores in the air and beneath the shingles. Similarly, removal of moss from the cracks in concrete surfaces is temporary as spores will inevitably be left behind or fly through the air which will permit regrowth within a short period of time. Mechanical removal of moss from grass is virtually impossible, at least without damaging the lawn and in most cases instead of removing the moss it is just being transplanted.

Various attempts have been made to control moss growth chemically, what I mean by chemically is that metals have been reduced to the salt form by the use of such acids as hydrochloric acid. Certain metallic salts, such as lead, iron, zinc, and copper-sulfur compounds, have been used with varying degrees of success but also with numerous drawbacks. Powdered compounds, such as copper sulfate, can be sprinkled dry on a roof; but the application is usually uneven and will burn, and as it washes off the roof it will kill grass, trees, plants and ornamental plants. It washes off within a few weeks or on the next rain and requires frequent reapplication. Water solutions of zinc or ferrous sulfate can be applied more evenly than the powders of such compounds but likewise require frequent reapplication and burn when they run off. Such solutions can also harm a person's skin, necessitating precautions during application. Ferrous sulfate has the further disadvantage that it stains concrete, roofs, tile and cloth surfaces. Such compounds are also unsuitable for lawns and gardens because they tend to burn the grass and garden plants, and one has to watch out not to get any on the walkways of concrete.

Lime is frequently used on grass and in gardens to suppress moss growth. However, it too stains concrete and so cannot be used on patios or on roofs because it would start rot. Moreover, it raises the pH of the soil which is undesirable for many applications.

Rooftops have also been treated with metal strips. For example, nailing a flat strip of copper to a roof has been tried but has proven unsatisfactory for treating established moss growths. It can take many months before natural erosion of the strips by rain releases enough metal ions to begin killing the moss. S. L. Rapaport has previously proposed, in U.S. Pat. No. 3,479,130, mounting flat bimetallic strips horizontally along a rooftop to inhibit microbial or fungal growths which darken rooftops in semitropical or tropical climates. Rapaport's bimetallic strips comprise two metals, such as copper and lead, between which an electrolytic reaction is said to result when rainwater contacts the metal. According to Rapaport, such reaction dissolves ions of the metals into the water to create a solution which kills the microbes and fungus. To obtain adequate coverage of a rooftop, multiple strips are vertically spaced four to ten shingles apart. However, it can take several months before any reduction in moss occurs, if any. Also, installing such strips is time-consuming and results in an aesthetically unappealing horizontally striped appearance of the roof, and the rain may not come into contact, or it may rain too much, or it may not rain enough or not at all.

My U.S. Pat. No. 4,276,732 describes a device for killing moss on rooftops comprising an elongated bimetallic trough for horizontal positioning along a rooftop to catch rainwater. The rainwater contacts layers or chips of copper and lead as it flows through holes at the top of the trough. The resultant electrolyte flows down the rooftop and kills the moss. Such a device is an improvement over Rapaport but is still aesthetically unappealing, expensive, and time-consuming to install.

None of the foregoing metal devices is usable on a horizontal surface; and so they cannot be used on lawns, patios, trees, sidewalks, or driveways. Practical considerations of the normal usage of such surfaces further preclude using strips or troughs on lawns, sidewalks, tree branches, sidewalks and the like.

In U.S. Pat. No. 3,494,727, Rapaport describes imbedding lead and copper chips of visible size into the surface of roofing shingles during manufacture. This procedure meets the aesthetics objection in the treatment of rooftop moss but would require re-roofing existing buildings at substantial expense, not to mention the increased cost of producing such roofing material. What if the metals rolled down over the roof? Moreover, this proposal is limited to treatment of rooftops with composition shingles and thus affords no solution to the problems of suppressing moss growths on other roofing materials, patios, trees, driveways, buildings and lawns.

Accordingly, a need remains for an effective method for killing moss on rooftops, building, lawns, trees, patios, sidewalks, and driveways which is inexpensive, easy to apply, fast-acting, long-lasting and additionally lacks the drawbacks of prior methods and also is not made from a chemical process of metals mixed with acids that form a salt that can burn and leach into the soil and burn roots.

SUMMARY OF THE INVENTION

It is a principal object of the invention to improve upon prior methods of controlling moss growth on buildings, rooftops, patios, driveways, sidewalks, trees, and in lawns and gardens.

Another object of the invention is to provide a universal method which will inhibit growth of moss on any of the foregoing surfaces for a year or more after a single application.

Yet another object of the invention is to provide a method for killing moss which is aesthetically inconspicuous.

A further object is to provide a moss-killing product which is inexpensive and easy to apply.

Another object of the invention is to provide a method for killing moss which can be used over all area where moss grows without any of the drawbacks of prior methods.

Another object of the invention is to provide a non-burning product unlike the others that are chemically broken down by acids into salts.

It is also an object of the invention to provide a product which will neither kill nor burn grass or garden vegetation or ornamental plants and trees, nor stain concrete, building and roofs or other man-made surfaces.

It is a further object to provide a method of application and a product which is safe for humans and animals, a product that will not burn or destroy vegetation, and therefore can be applied without taking special precautions.

According to the invention, a moss-killing powder is disclosed which can be applied in dry form to a moss-covered surface, such as in a shaker can by sprinkling or by adding the contents to water and making a slurry and then sprinkling onto the infested moss area. To make the powder, an atomized elemental metal is selected from a group of metals which dissolve in water in minute concentrations to form a biocidal solution effective to kill moss. Such metal is atomized, powdered to invisible particle sizes 25 microns to 0.5 microns in size, and mixed in predetermined proportions with a talc-like, very fine 80 to 100 microns carrier material such as silica clay. Besides diluting and uniformly dispersing the atomized powdered metal particles in the resulting mixture and preventing caking of the atomized metal powder, the carrier material preferably has the characteristic that the fine atomized metal particles adhere to the surface of the carrier silica clay and are thereby reliably conveyed to the surface to be treated. The carrier material also preferably holds the adhering particles in close proximity to each other on the treated surface to encourage galvanic reaction upon contact with water when two different metals are used. Silica clay is a carrier material which provides such characteristics; and, additionally, silica clay powder quickly becomes wet and helps disintegrate when contacting water by absorbing water.

A metal and carrier mixture according to the present invention is sprinkled uniformly in dry form on the surface to be treated. It is preferable to apply the product mix by adding water and making a slurry and then sprinkling the slurry onto the infested moss area. Although in dry form, apply the dry powder to a water wetted surface to promote initial adherence to the surface, thereby preventing displacement of the powder by the wind and also starting its action immediately. Upon contact with water, the carrier absorbs water and slowly disintegrates into a semifluidic yet cohesive mass, and wets the adhered metal particles to start dissolving the metal to produce the biocidal solution which kills moss. The fine atomized metal powder and biocidal solution permeate the cracks and crevices of the moss-covered surface, thus killing spores and hidden moss which have not yet reached the surface. Over time, the silica clay carrier material itself disperses and washes away. By using a carrier ingredient, such as silica clay, which starts to disperse when wetted, the application is essentially invisible to the naked eye and would need a microscope to be seen and identified.

Dissolution of the metal particles is preferably enhanced by using at least two finely atomized powdered elemental metals which react galvanically in the presence of water or moisture, such as copper and zinc. With such a combination, biocidal ions are dissolved more quickly into the water. The metals are preferably mixed in proportion to their relative efficacies against moss and mildew; i.e. more of the more effective metal would be utilized. Prompt generation of a biocidal solution is greatly enhanced by the large relative surface area provided by the fine atomized metal particles. Yet the relatively low solubility of the atomized elemental metals in water prevents their immediate dissolution, enabling moss growth to be inhibited for a year or more after a single application. This feature is preferably enhanced by adjusting the relative sizes of the different metal particles to their solubilities, that is, using small particles of the more soluble metal.

The foregoing product can be applied with equal effect and absence of drawbacks to lawns, gardens and trees, as well as buildings, rooftops, patios, and the like. Alternatively, in a second embodiment of the invention, the atomized powdered metal or metals can be mixed with a dry granular fertilizer, which serves as the carrier, for application to lawns and gardens. Neither burning of vegetation nor changes in soil pH are caused by the metal constituents of the mixture, while it effectively controls moss.

The foregoing, and other objects, features, and advantages of the invention will become more readily apparent from the following detailed description of two preferred embodiments.

DETAILED DESCRIPTION

The preferred embodiment utilizes copper and zinc as the active ingredients. Such metals are selected primarily because they are both effective in very low concentration with water solutions to kill moss growing on surfaces exposed to the atmosphere and will react galvanically in water to enhance dissolution. In addition, I have discovered that such metal ion solutions will not kill other desired lawn or garden growth; my product stays on the surface where the moss is (whereas other products either wash off or leach down to the roots and burn), and will not stain roofs, concrete, or other man-made surfaces, will not irritate human skin, will not leach into the soil quickly or wash off, and has clinging and staying power on the surface, unlike the salts that leach away quickly with the first rain or moisture, and this new product is relatively inexpensive.

The elemental zinc is atomized powdered to about 25 microns to 0.50 microns. The elemental copper is atomized powdered to about 15 microns to 0.5 microns. The two powders are then mixed in about a 9 to 1 ratio, by weight, respectively, by either shaking or tumbling in a tightly sealed container like a cement mixer, thus creating a uniform mixture of the metal particles. The foregoing sizes and proportions can be varied. However, the larger particle size and proportions of zinc are preferred because I have discovered that the solubility in water and the biocidal efficacy of zinc are as good as those of copper and safer. A mixture of the foregoing particle sizes and proportions is effective to control moss for about one year when applied uniformly at a rate of about one ounce per 250 square feet of surface area.

Next, a fine silica clay is granularized to 80 to 100 microns powder in size. This size is effective to blending of the atomized metals and to resist being carried by the wind when spread dry.

The fine grain powder carrier ingredient and the atomized powdered metal active ingredient are then combined in a 3 to 1 ratio, by weight, respectively, in an airtight container and therein thoroughly mixed by shaking or tumbling the mixture. During the mixing process, a substantial proportion of the fine metal particles adhere to the carrier surfaces. Combining this atomized powdered metal active ingredient with the carrier ingredient in these specified proportions will create a moss-killing powder which will effectively cover 250 square feet per four ounces of the resultant powder mixture.

The moss-killing powder mixture is applied in dry or wet form to the surface to be treated. With a dry application, apply the product after a rain or after watering. The moss killer may be sprinkled uniformly in dry or wet form over a moss-covered surface from a suitable spreading device such as a shaker can or a sprinkler container device.

In a second embodiment, the metal active ingredient of the same proportions of zinc and copper powder as described above is mixed with a specified proportion of a carrier ingredient consisting of either lawn or garden fertilizer. In one example, one ounce of the powdered metal active ingredient is mixed into each of 5 pounds of nitrogen-phosphorus-potash lawn fertilizer for covering 250 square feet of lawn area. Such fertilizer has a granularity range of about 15 to 30 mesh. Such mixture is effective to kill moss growing in the grass, but the metal powder constituent does not injure the grass or adversely affect soil pH.

The ion-producing and biocidal characteristics of the active ingredient may alternatively be enhanced by utilizing other combinations of elemental metals from the following list; copper, zinc, aluminum, iron, cadmium, lead, nickel, and tin. Since highly refined metals are not required, traces of the other metals are typically found in the foregoing zinc and copper powder mixture. In one operative example, the active metal ingredients are, by weight; zinc—86.5%; copper—9.9%; zinc-oxide—3.1%, and the balance comprises 0.1% or less each of lead, iron, cadmium and cadmium oxide.

Other ingredients may be used for the carrier. Granularized corncob and walnut shells are very good, but fine silica clay is the preferred carrier ingredient as it will better adsorb and cling the metal particles to its surface and hold them while the clay is wet with water and until the product is applied to the infested moss area. Thereupon, the silica clay soaks up the water and starts the galvanic action of the atomized metal ions and holds the metal particles in close proximity for a time. Then, the silica clay gradually disperses slowly and disappears. Dry fertilizer has essentially similar characteristics when applied to lawns in a mixture containing powdered elemental metals.

Having illustrated and described the principles of the invention in two preferred embodiments, it should be apparent to those skilled in the art that the invention may be modified in arrangement and detail without departing from such principles. I claim as my invention all such modifications as come within the true spirit and scope of the following claims.

I claim:

1. A moss control composition consisting essentially of atomized elemental zinc and atomized elemental copper in a ratio sufficient such that said zinc and said copper, when wetted, react to produce a biocidal solution effective to kill moss; and a carrier material selected such that the metal particles will cling to the surface of said carrier material.

2. A composition according to claim 1 in which the carrier material is fine silica clay.

3. A moss-controlling composition consisting essentially of atomized elemental zinc and atomized elemental copper, in a ratio of about 9:1, said zinc having a particle size of about 24 to 0.5 microns and said copper having a particle size of about 15—0.5 microns, combined with fine silica clay, such that the weight ratio of the clay to the metals is about 3:1.

4. A method for controlling moss by applying to a moss infested surface, an effective amount of the composition of claim 1.

5. A method of controlling moss by applying to a moss infested surface an effective amount of the composition of claim 2.

6. A method for control of moss by applying to a moss infested surface an effective amount of the composition of claim 3.

7. A method according to claim 6 in which the application rate is one ounce composition per 250 square feet of surface.

* * * * *